US006451541B1

(12) United States Patent
Winnacker et al.

(10) Patent No.: US 6,451,541 B1
(45) Date of Patent: Sep. 17, 2002

(54) CHAPERONES CAPABLE OF BINDING TO PRION PROTEINS AND DISTINGUISHING THE ISOFORMS PRP$^C$ AND PRP$^{SC}$

(76) Inventors: Ernst-Ludwig Winnacker, Dall'Armistr. 41a, 80638 München (DE); Stefan Weiss, Blütenstr. 20, 80799 München (DE); Frank Edenhofer, Westendstr. 141, 80339 München (DE); Roman Rieger, Römerstr. 43, 82362 Weilheim (DE)

( * ) Notice: Subject to any disclaimer, the term of this patent is extended or adjusted under 35 U.S.C. 154(b) by 0 days.

(21) Appl. No.: 09/180,652
(22) PCT Filed: May 13, 1997
(86) PCT No.: PCT/EP97/02444
§ 371 (c)(1),
(2), (4) Date: Nov. 12, 1998
(87) PCT Pub. No.: WO97/43649
PCT Pub. Date: Nov. 20, 1997

(30) Foreign Application Priority Data

May 14, 1996 (DE) ............................................. 96107677

(51) Int. Cl.$^7$ ...................... G01N 33/53; G01N 33/566; C12P 21/04; A61K 39/395; C07K 1/00
(52) U.S. Cl. .................. 435/7.1; 424/130.1; 424/139.1; 424/185.1; 424/192.1; 435/70.1; 435/70.2; 435/71.1; 436/501; 436/503; 436/518; 436/528; 436/547; 530/350; 530/387.1
(58) Field of Search ............................ 424/130.1, 139.1, 424/185.1, 192.1; 435/7.1, 70.1, 70.2, 71.1; 436/501, 503, 518, 528, 547; 530/350, 387.1

(56) References Cited

PUBLICATIONS

Ivanyushina, V.A., et al, "Molecular chaperones: Novel proteins, novel functions (Review)", Molecular Biology, vol. 25, No. 4, Part 1, pp. 679–689, Jul. 3, 1991.*

Wynn, R.M., et al, "Molecular chaperones: Heat–shock proteins, foldases, and matchmakers", J. Lab. Clin. Med., vol. 124, pp. 31–36, Jul. 1, 1994.*

DeFranco, D.B., et al, "Molecular chaperones and subcellular trafficking of steroid receptors", J. Steroid Biochem. Molec. Biol., vol. 65, No. 1–6, pp. 51–58, Jan. 1, 1998.*

Craig, E.A., et al, "heat shock proteins: Molecular chaperones of protein biogenesis", Microbiological Reviews, vol. 57, No. 2, pp. 402–414, Jun. 1, 1993.*

Liautard, J.–P., "Are prions misfolded molecular chaperones?", FEBS Letters, vol. 294, No. 3, pp. 155–157, Jul. 3, 1991.*

* cited by examiner

Primary Examiner—Rodney P Swartz
(74) Attorney, Agent, or Firm—Roylance, Abrams, Berdo & Goodman, L.L.P.

(57) ABSTRACT

The present invention relates to methods for the detection or isolation of prion proteins by use of chaperones specifically binding to said proteins. The invention further relates to a method for in vitro diagnosis of a transmissible spongiform encephalopathy and to pharmaceutical compositions, preferably for the prevention or treatment of said disease.

18 Claims, 4 Drawing Sheets

Figure 1:
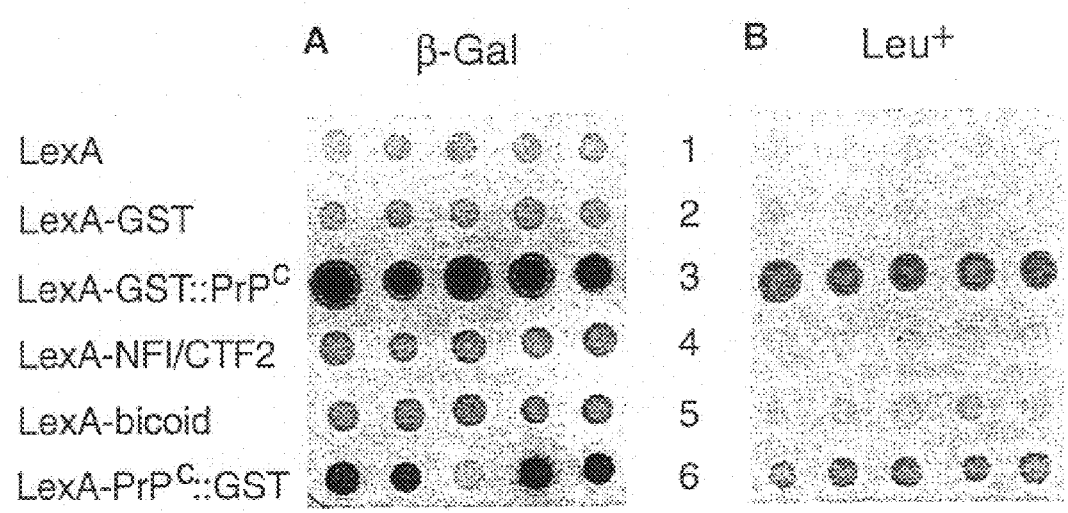

CHAPERONES CAPABLE OF BINDING TO PRION PROTEINS AND DISTINGUISHING THE ISOFORMS PRP$^C$ AND PRP$^{SC}$

The present invention relates to methods for the detection or isolation of prion proteins by use of chaperones specifically binding to said proteins. The invention further relates to a method for in-vitro diagnosis of a transmissible spongiform encephalopathy and to pharmaceutical compositions, preferably for the prevention or treatment of said disease.

Transmissible spongiform encephalopathies (TSEs) are neurodegenerative diseases such as scrapie of sheep, bovine spongiform encephalopathy (BSE) of cattle and Creutzfeldt-Jakob disease (CJD) of man (34). Infectious preparations derived from infected brains are resistant to ultraviolet and ionizing radiation as well as other procedures which inactivate nucleic acids indicating that nucleic acids may not be required for infectivity. Purification of infectious preparations from brains revealed the presence of a protein required for infectivity (36). These experimental observations led to the 'protein only' hypothesis, which proposes that proteinaceous infectious particles ('prions') are responsible for the transmission of TSEs (3, 4, 36). Prions consist mainly of a protease resistant protein designated PrP$^{Sc}$ (prion protein, 'Sc' for scrapie), a posttranslationally modified form of the proteinase K sensitive host encoded PrP$^c$ ('c' for cellular) (8, 9, 11, 34). Both isoforms share the same amino acid sequence, but differ in their secondary structure (31, 42). Circular Dichroism (CD) and Fourier Transform Infrared (FTIR) spectroscopy revealed a significantly higher β-sheet content for PrP$^{Sc}$ as compared to a high α-helix content in PrP$^c$ (17, 31, 38). Structural predictions of PrP$^c$ led to a model which proposed that four domains between amino acid residues 109 to 122, 129 to 141, 178 to 191 and 202 to 218 form α-helices (24). It has been suggested that prion propagation involves the conversion of α-helical domains in PrP$^c$ into β-sheets in PrP$^{Sc}$ (26, 30, 31). The in vitro conversion of PrP$^c$ into PrP$^{Sc}$ was demonstrated employing a proteinase K resistance assay (28). A modified model was recently suggested according to which PrP$^c$ must be partially unfolded and refolded into PrP$^{Sc}$ under the direction of an oligomeric PrP$^{Sc}$ seed (29). This model provides explanations for scrapie species barriers (27) and strain-specific properties of prions (7). In addition, experiments employing transgenic mice led to the proposal that prion propagation requires a species-specific macromolecule designated 'protein X' (43).

So far, there is no method described allowing the straightforward detection or isolation of natural prion proteins. The isolation of PrP$^c$ described in the prior art (31) is time consuming, ineffective and yields only minimum amounts of protein. The isolation of PrP$^{sc}$ described in the prior art (31, 35, 64) is also time consuming and ineffective and the purity of the PrP$^{sc}$ is speculative. Furthermore, up to now it was not possible to discriminate between the cellular isoform PrP$^c$ and the isoform PrP$^{sc}$ or PrP27–30, which is a prerequisite for the development of a simple and reliable assay for diagnosing a transmissible spongiform encephalopathy.

Tatzeh et al., PNAS USA 92 (1995), 2944–2984, investigate proteins that might feature in the conversion of the cellular prion protein (PrP$^c$) into the scrapie isoform (PrP$^{sc}$). It was found that in scrapie-infected N2a cells the expression and subcellular translocation of specific heat shock proteins was altered. However, said document does not disclose that chaperones like the heat shock proteins specifically bind to prion proteins and, thus, can be used to detect or isolate prion proteins.

Therefore, the technical problem underlying the present invention is to provide a simple method for the efficient isolation of prion proteins and the detecion of said proteins, preferably in a way that allows for discrimination between different isoforms of PrP.

The solution to said technical problem is achieved by providing the embodiments characterized in the claims.

Thus, the present invention relates to a method for the detection of a prion protein comprising the steps of:
(a) contacting a probe suspected to contain a prion protein with a chaperone, and
(b) determining whether a prion protein binds to the chaperone.

In addition, the present invention relates to a method for the isolation of a prion protein comprising the steps of:
(a) contacting a probe containing a prion protein with a chaperone, and
(b) isolating the chaperone-bound protein from the chaperone.

When carrying out experiments in order to identify proteins capable of interacting with PrP$^c$ it was surprisingly found that chaperones are capable of specifically binding to prion proteins. The specificity of the observed in vivo interactions was confirmed by in vitro binding studies employing recombinant prion proteins. Mapping of the interaction site between the molecular chaperones and PrP$^c$ was performed using recombinant prion GST-fusion peptides. The results show that a GST-PrP$^c$ fusion protein binds specifically to Hsp60 in an *S. cerevisiae* environment as well as in vitro. The Hsp60 family is one of the best characterized members of the molecular chaperones which mediate ATP-dependent folding of polypeptide chains (13, 18, 22, 23) and which are widely distributed and conserved between prokaryotes and mammals. Human Hsp60 (544 amino acids) is proposed to form tetradecameric complexes in vivo as shown in the crystal structure of the prokaryotic homologue GroEL (10). The cDNAs isolated by a two-hybrid screen in *S. cerevisiae* (15, 19, 21) encode N-terminally truncated proteins of 399, 317 and 246 amino acids in length, comprising at least in part the apical domain of the Hsp60 monomer. This apical domain contains several amino acid residues which specifically mediate peptide binding in the case of GroEL (14). Specificity of the PrP$^c$/Hsp60 interaction in vivo was confirmed employing the 'false baits' LexA-bicoid and LexA-NFI/CTF2 as well as authentic LexA and LexA-GST. The interaction was confirmed in vitro using recombinant GST-PrP$^c$ and recombinant full-length Hsp60 as well as GroEL. This result shows that the PrP$^c$/Hsp60 interaction does not involve additional factors and that thus, chaperones can be used for the detection and isolation of prion proteins. The recombinant rPrP27–30 (47) represents the proteinase K sensitive isoform of the proteinase K resistant core PrP27–30 isolated from scrapie preparations. The results of the in vitro interaction between rPrP27–30 and Hsp60 reveal that the core region of PrP (amino acids 90 to 231) is sufficient for binding to Hsp60.

Identification of the interaction site between amino acid 180 and amino acid 210 by mapping of PrP$^c$ peptides showed that binding of Hsp60 to PrP$^c$ occurs within a highly conserved region of the prion protein containing amino acids 180, 198, 200 and 210. Mutation of these residues segregate with inherited prion diseases in humans (33). In addition, the chaperone-binding fragment GST::P180–210 contains at least in part the two putative α-helical domains H3 (amino acids 178 to 191) and H4 (amino acids 202 to 218) (24). The conversion of α-helical regions into β-sheets of PrP are thought to be responsible for PrP$^{Sc}$ formation. There are several possibilities to suggest a possible physiological relevance of the Hsp60/PrP interaction. (i) Hsp60 might be involved in the propagation of $PrP^{Sc}$ as has been shown for the interaction of the yeast prion-like factor [psi$^+$] with the molecular chaperone Hsp104 (12, 50). Based on studies with transgenic mice, it has been suggested recently that a species-specific macromolecule, designated 'protein X', participates in prion formation (43). Protein X was proposed to function as a molecular chaperone facilitating the transformation of PrP isoforms. This unknown factor 'X' might in fact be Hsp60. (ii) Alternatively, Hsp60 could prevent aggregation of $PrP^c$ to $PrP^{Sc}$ amyloids e.g. by trapping misfolded forms of $PrP^c$.

More recent data suggested that so-called "chemical chaperones" such as glycerol, trimethylamine N-oxide (TMAO), and dimethylsulfoxide (DMSO) interfere with $PrP^{Sc}$ formation by stabilizing the α-helical conformation of $PrP^c$. (67)

The detection or isolation of prion proteins by the methods of the invention relates to recombinantly produced prion proteins or prion proteins from natural sources. Prion proteins can be extracted from natural sources, for example, by the method described in (31, 64); involving suspending tissue in sucrose, homogenization and clarification by centrifugation.

Contacting the probe suspected to contain a prion protein with a chaperone can be carried out by known methods, for example, with the chaperone being in solution or being immobilized, for example on a matrix such as a gel or a resin for chromatography (66).

Contacting of the probe with the chaperone and analyzing of the complex chaperone-prion protein can also be carried out as described in the Examples below.

Suitable chaperones which specifically bind to prion proteins can be inter alia determined by the person skilled in the art by assaying the binding of a particular chaperone to prion proteins as described in the Examples, below.

In one preferred embodiment of the method of the invention, a fragment, analogue or derivative of said chaperone is used which is still capable of binding the prion protein.

As used herein, the term "derivative" refers to such derivatives which may be prepared from the functional groups which occur at side chains on the residues or the N- or C-terminus groups, by means known in the art.

The term "fragment" relates to any fragment of the chaperone which still has the capability to interact with the prion protein and such a fragment can be prepared by techniques known to the person skilled in the art.

In another preferred embodiment of the invention, the chaperone used in the method for detection and/or isolation of a prion protein is Hsp60 or GroEL.

In a further preferred embodiment the chaperone is a recombinant protein, i.e., the chaperone is produced by recombinant DNA technology, namely by expression from a cloned DNA sequence.

In a still further preferred embodiment, the chaperone is part of a fusion protein, which can comprise, besides the chaperone a protein or preferably, a protein domain which confers to the fusion protein a specific binding capacity. Preferably, the recombinant chaperone is fused to glutathione-S-transferase.

Any prion protein, isoform, fragment or derivative of such prion protein or mixture of said substances can be detected or isolated by the method of the invention as long as it is capable of being bound by the chaperone. In a preferred embodiment the prion protein to be detected or isolated is the prion protein $PrP^c$ and/or an isoform of $PrP^c$. Preferably the prion protein isoform is the isoform $PrP^{sc}$ or a fragment or derivative thereof.

In a further preferred embodiment the prion protein is the processed form $PrP^c$23–231 comprising amino acids 23 to 231 of $PrP^{sc}$ and/or the isoform $PrP^{sc}$ is the N-terminally truncated derivative PrP27–30 or a fragment thereof.

As already stated above, for determining whether a prion protein was bound to a chaperone, the chaperone can be in solution or be attached to a solid phase.

Following incubation of both participants in solution, the interaction can be proved by co-immunoprecipitation (51) followed by Western Blotting (44) employing a PrP specific antibody as described, for example, in (20), a chaperone-specific antibody or an antibody directed against one of the Tags, i.e. GST-antibody, FLAG-antibody, BTag-antibody, antibody directed against the calmodulin binding protein, the S-peptide, the maltose-binding-protein, oligohistidine and the green fluorescent protein (GFP). Furthermore, the interaction can, for example, be proved by (i) crosslinking employing reagents such as dimethylsuberimidate (52), (ii) by affinity chromatography (66) by adding the immobilized ligand directed against one of the tags fused to one of the two partners (Criss-Cross interactions), or (iii) by analyzing the complex by a non-denaturing polyacrylamide gel (53) or by a size exclusion chromatography which is mostly HPLC/FPLC (54).

In a preferred embodiment, the chaperone is in solution and detectably labelled. The person skilled in the art will know suitable labels or will be able to ascertain such labels using routine experimentation. Preferably the detectable label is selected from a radioisotope, a fluorescent compound, a colloidal metal, a chemiluminescent compound, a bioluminescent compound, a phosphorescent compound or an enzyme.

Alternatively, the chaperone is bound to a solid phase for the detection and/or isolation of a prion protein. Suitable materials are known to the person skilled in the art and include, for example, a gel or a resin (Sepharose, agarose, nitrocellulose, dynabeads®, polystyrene etc.).

In a preferred embodiment, the solid phase is a matrix comprising glutathione, such as glutathione-sepharose. The protein domain used for binding of the chaperone to a matrix can also be an oligohistidine (55), Calmodulin binding peptide (CBP) (56), S-peptide (ribonuclease A) (57), FLAG (58), green-fluorescent protein (GFP, 65), BTag (59), or maltose-binding-protein (MBP; 61). The tagged chaperone can be immobilized to gluthathione, IMAC-$Ni^{2+}$. Calmodulin, S-protein 104 aa (57), anti-FLAG-antibodies, anti GFP-antibodies, BTag-antibodies (59) or maltose (60).

Alternatively, coupling of the chaperone itself by the fusion protein can be done via thiol-groups of non-oxidized cysteins or, alternatively, via free lysine or $\alpha$-amino groups to cyanogen bromide agarose or a-hydroxy succinimide activated agarose (63).

Regarding the interaction of the prion proteins with chaperones where one of the compounds is immobilized, the interaction can be determined by IASYS (FISONS). Protein-protein interactions can be detected and measured by biosensors, which use the evanescent field to probe biomolecular mass and concentration close to the probe surface. Alternatively, such interaction can be determined by far western blot/affinity blot (62): the prion-protein either tagged or untagged or the chaperone either tagged or untagged are blotted onto a membrane such as nitrocellulose or PVDF. The other interaction partner either the tagged/untagged prion protein or the tagged/untagged chaperone in solution is incubated with the protein associated membrane.

Interaction is confirmed by addition of an antibody directed against the protein in solution itself or the tag fused to the protein (62).

In a still further preferred embodiment of the method of the invention for isolating prion proteins, the chaperone is part of a matrix contained within an affinity chromatography column (63, 66) and step (b) is modified in such a way that (i) the probe suspected to contain the prion protein is passed through the column, (ii) after washing, the prion protein is eluted from the column, optionally by a change in pH or ionic strength and collected; and (iii) optionally the collected prion protein is further purified.

By this kind of affinity chromatography which is, for example, described in (55, 63, 66), impurities contained in the prion protein preparation are passed through the column. The prion protein(s) will be bound to the column by the chaperone. Suitable conditions for allowing the specific binding of the prion protein to the column and for eluting the prion protein from the gel can be determined by the person skilled in the art and are, for example, described in (47, 48).

In an alternative embodiment, the isolation of the prion protein is carried out as a batch process according to standard procedures or, for example, by using a modified version of the procedure described in the Examples, below, wherein instead of the prion protein, the chaperone is attached to glutathione-Sepharose beads, for example, gluthathione-Sepharose 4B beads.

Prion proteins isolated and purified according to the method of the invention can be used, for example, as immunogen for raising antibodies, as active component of pharmaceutical compositions or for the development of diagnostic assays, such as ELISA.

The probe can be obtained from various organs, preferable from tissue, for example brain, ileum, cortex, dura mater, purkinje cells, lymphnodes, nerve cells, spleen, tonsils, muscle cells, placenta, pancreas, eyes, backbone marrow or peyer'sche plaques from a body fluid, preferably from blood, cerebrospinal fluid, semen or milk.

As is evident from the results presented in Example 6, binding of the chaperone GroEL is stronger to rPrP27–30 compared to $PrP^c$ (see lane 3 of FIG. 2B versus lane 2 of FIG. 2C). These results were confirmed by further titration experiments with GroEl and Hsp60 (data not shown). Thus, determining the strength of binding of a chaperone with the prion protein in a probe by comparing it with the strength of binding of the same chaperone with $PrP^{sc}$ (or rPrP27–30) and $PrP^c$ standards allows the determination of whether a prion protein indicative for transmissible spongiform encephalopathy (TSE) is contained in a sample.

Accordingly, a further preferred embodiment of the invention relates to a method for the in-vitro diagnosis of a transmissible spongiform encephalopathy, wherein step (b) is modified in such a way that the differences in binding of the chaperone to $PrP^c$ and an isoform of $PrP^c$, respectively, preferably $PrP^{sc}$, are used to determine whether an isoform of $PrP^c$ is present in the probe or not.

The present invention furthermore provides a complex of the chaperone and a prion protein and, in addition, a composition for the detection and/or isolation of a prion protein comprising a chaperone as defined above.

Furthermore, the present invention relates to a diagnostic composition comprising the chaperones as defined above. Such compositions may contain additives commonly used for diagnostic purposes. Said compositions can be used for the diagnosis of transmissible spongiform encephalopathies by applying the approach described above, wherein a probe taken from a body is incubated with a chaperone and the strength of binding of the chaperone to the prion protein contained in the probe is determined. In the case that brain is used as a probe, diagnosis is often carried out post mortem but is, in certain cases, also possible on the living organism (biopsy). In the case that blood, milk or cerebrospinal fluid is used as a probe, diagnosis is possible for living individuals.

In another embodiment, the present invention relates to a pharmaceutical composition comprising a chaperone as defined above or, alternatively, comprising a substance that inactivates said chaperone. Such compositions can optionally comprise pharmaceutically acceptable carriers.

Since, for example, chaperones like Hsp60 are assumed to be capable of preventing the aggregation of $PrP^c$ to $PrP^{sc}$, it might be possible to block the conversion of the isoform $PrP^c$ into the prion associated isoform $PrP^{sc}$ by administration of such chaperones which specifically bind prion proteins and, thus, to prevent or treat transmissible spongiform encephalopathy.

On the other hand, it might be possible that chaperones are involved in the transformation of $PrP^c$ to $PrP^{sc}$. Thus, blocking such transformation by the administration of agents which specifically inactivate such chaperones which specifically interact with prion proteins could also be helpful for the treatment or prevention of transmissible spongiform encephalopathies. Such substances can be selected by the person skilled in the art by routine experimentation and include ligands that bind to the chaperone, thus preventing the interaction of the chaperone with the prion protein. Examples of such ligands are antibodies, preferably monoclonal antibodies, or a fragment of a protein which a domain responsible for binding to the chaperone, e.g. a fragment of $PrP^c$ containing amino acids 180 to 210.

Preferably, said compositions are used for the prevention or treatment of transmissible spongiform encephalopathy, for example, Scrapie, bovine spongiform encephalopathy (BSE), Creutzfeld-Jacob Disease (CJD), Gerstmann-Sträußler-Scheinker-Syndrome (GSS), Kuru, fatal familial insomnia (FFI) or transmissible mink encephalopathy (TME).

LEGENDS TO THE FIGURES

FIG. 1: Identification of $PrP^c$23–231/Hsp60 interaction employing the two-hybrid system.

Two different phenotypes confirm this interaction. Yeast cells containing the reporter plasmid pSH18–34 were cotransformed with the pJG4–5 plasmid carrying the cDNA clone encoding for Hsp60 (amino acids 146–544) and the bait plasmids pSH2-1 (row 1), pSH2-1-GST (row 2), pSH2-1-GST-$PrP^c$ (row 3), pSH2-1-NFl/CTF2 (row 4) (49), pEG202-bicoid (row 5) (21) and pSH2-1-$PrP^c$-GST (row 6). Five of each transformants were resuspended in TE, dotted on galactose plates either supplemented with X-Gal (A) or leucine deficient (B) and incubated at 30° C. for 5 days.

Figure 2:
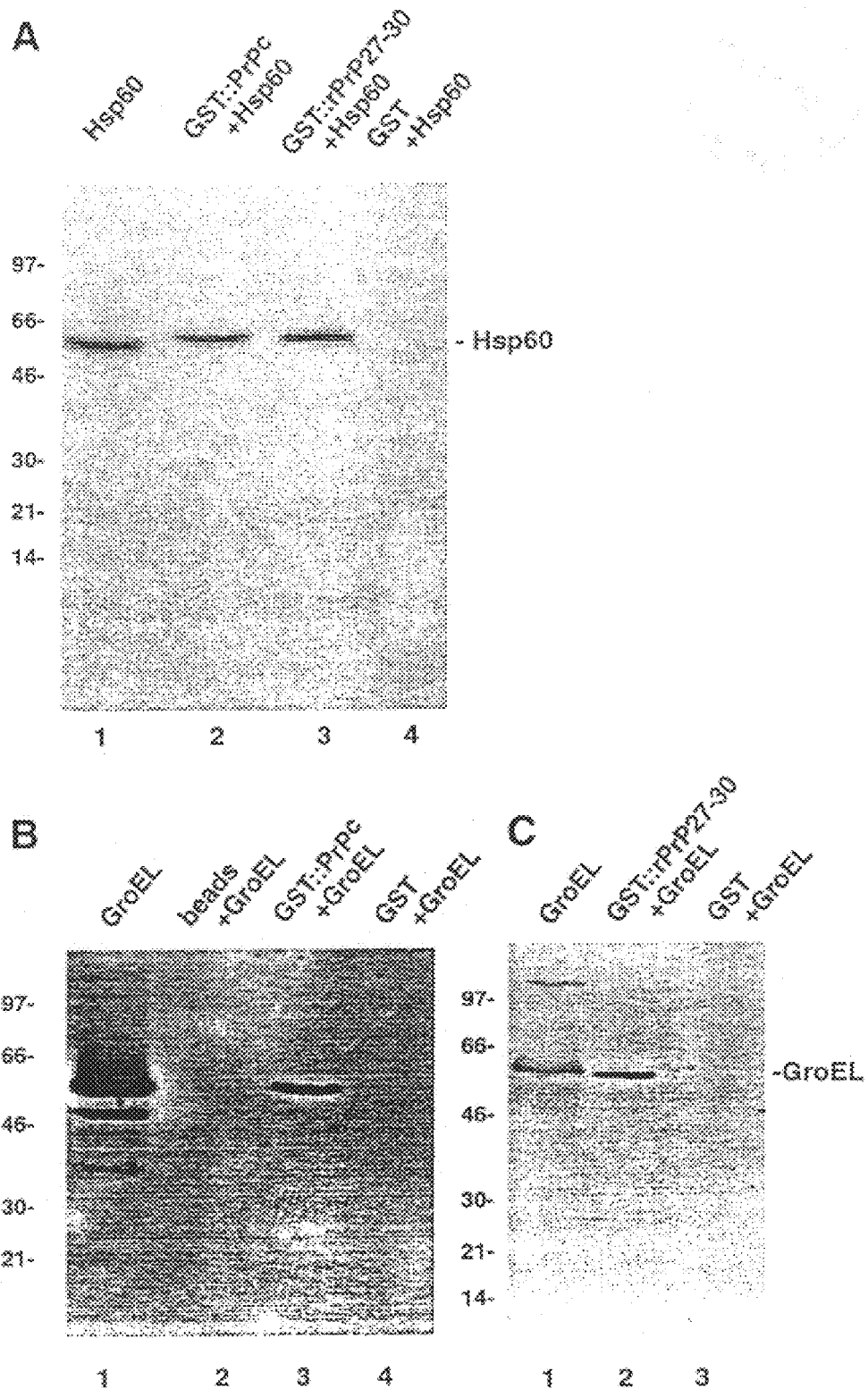

FIG. 2.: Immunoblot analysis of pull-down assays to demonstrate the in vitro interaction of Hsp60 and GroEL in the presence of PrP fused to GST.

Numbers on the left side indicate size in kDa. (A) Recombinant GST (1 mg), GST-rPrP27–30 (2 mg) as well as GST-$PrP^c$ (2 mg) immobilized on glutathioneSepharose were incubated with 10 mg Hsp60. After centrifugation beads were washed and resuspended in sample buffer. 4 ml each of GST-$PrP^c$ (lane 2), GST-rPrP27–30 (lane 3) and GST (lane 4) as well as 200 ng Hsp60 as a control (lane 1) were analyzed by SDS-PAGE (12.5%) and immunoblotting (PVDF) employing a monoclonal mouse anti-Hsp60 antibody and chemiluminescence detection. (B) Recombinant GST (1 mg) and GST-PrP$^c$ (2 mg) immobilized on glutathione-Sepharose as well as glutathione-Sepharose alone were incubated with 25 mg GroEL. After washing beads were resuspended in sample buffer. 4 ml each of a 1:1 slurry of beads (lane 2), GST-PrP$^c$ (lane 3) and GST (lane 4) as well as 2 mg GroEL as a control (lane 1) were analyzed on a 12.5% SDS get and blotted on a NC membrane. Protein detection was performed employing an anti-GroEL antibody and chemiluminescence. (C) Recombinant GST (1 mg) as well as GST-rPrP27–30 (2 mg) immobilized on glutathione-Sepharose were incubated with 25 mg GroEL. After washing beads were resuspended in sample buffer. 4 ml each of GST-rPrP27–30 (lane 2) and GST (lane 3) as well as 1 mg GroEL as a control (lane 1) were analyzed by SDS-PAGE and immunoblotting employing an anti-GroEL antibody and chemiluminescence.

Figure 3:
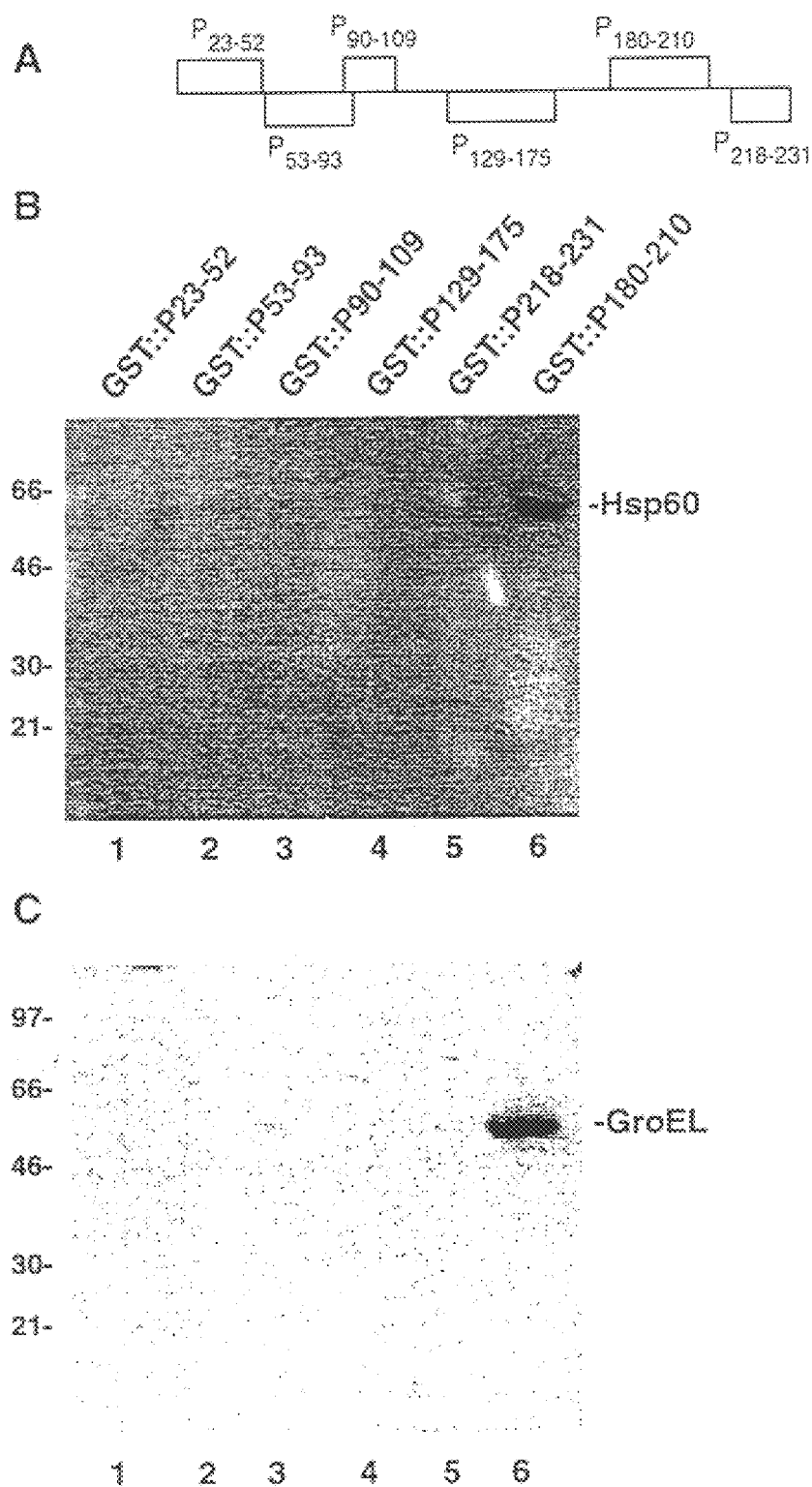

FIG. 3: Mapping the PrP$^c$/GroEL interaction site using fragments of PrP$^c$ as fusions with GST.

(A) Six fragments of PrP$^c$ were designed on the basis of biochemical predictions such as hydrophilicity, antigenicity and secondary structures and represent amino acids 23 to 52, amino acids 53 to 93, amino acids 90 to 109, amino acids 129 to 175, amino acids 180 to 210 and amino acids 218 to 231 (48). (B) Mapping analysis of the PrP/Hsp60 interaction site using the six GST fused PrP fragments. 2 mg each of the fragments bound to glutathione-Sepharose were incubated with 10 mg Hsp60. The beads were washed and resuspended in sample buffer. 4 ml each of the fragments GST::P23–52 (lane 1), GST::P53–93 (lane 2), GST::P90–109 (lane 3), GST::P129–175 (lane 4), GST::P218–231 (lane 5) and GST::P180–210 (lane 6) were analyzed on a 12.5% SDS gel and blotted onto a PVDF membrane followed by development employing an anti-Hsp60 antibody and chemiluminescence. (C) Mapping analysis of the PrP/GroEL interaction site. 2 mg each of the fragments bound to glutathione-Sepharose were incubated with 10 mg GroEL. The beads were washed and resuspended in sample buffer. 4 ml each of the fragments GST::P23–52 (lane 1), GST::P53–93 (lane 2), GST::P90–109 (lane 3), GST::P129–175 (lane 4), GST::P218–231 (lane 5) and GST::P180–210 (lane 6) were analyzed on a 12.5% SDS gel and blotted (PVDF). GroEL was detected by chemiluminesence using an anti-GroEL antibody.

Figure 4:
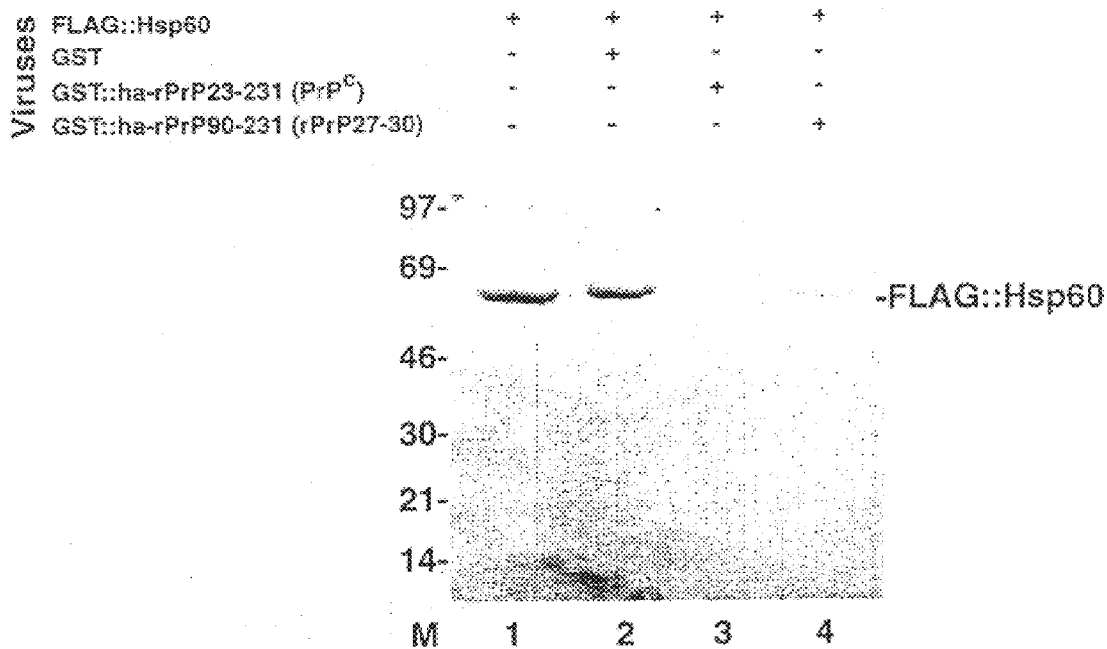

FIG. 4: Co-Expression of FLAG-tagged Hsp60 and GST-tagged prion proteins from Syrian golden hamster in the baculovirus system.

Cell lysates were analyzed on 12.5% SDS gel. Western Blotting employing an anti-Hsp60 antibody (Sigma Catalogue # H 4149) antibody shows decreased levels of FLAG::Hsp60 when co-expressed with GST::haPrP$^c$23–231 (lane 3) and GST::haPrp90–231 (lane 4) compared to FLAG::Hsp60 expression (lane 1) and co-expression of GST control (lane 2).

The following examples illustrate the invention:

EXAMPLE 1
Construction of Vectors

Construction of yeast vectors. Cloning procedures were performed as described previously unless otherwise stated (40). The shuttle vectors pSH2-1 and pEG202, which direct the synthesis of different LexA hybrids (amino acids 1–87 and amino acids 1–202) (19, 21), were used to construct the LexA fusion 'baits'.

(i) Construction of pSH2-1/pEG202-GST. A 666-bp DNA fragment coding for glutathione S-transferase (GST) was amplified by PCR (39) from the cDNA clone pAcSG2T::PrP$^c$23–231 (48). The fragment was subcloned into plasmids pSH2-1 and pEG202 using the EcoRI/BamHI restriction sites, resulting in the vectors pSH2-1/pEG202-GST.

(ii) Construction of pSH2-1/pEG202-PrP$^c$. A 646-bp DNA fragment containing nucleotides coding for amino acids 23 to 231 of the Syrian golden hamster Prp$^c$ protein was amplified by PCR from the cDNA clone pAcSG2T::PrP$^c$23–231. The PrP$^c$ cassette was cloned via EcoRI/BamHI restriction sites into vectors pSH2-1 and pEG202, yielding pSH2-1/pEG202-PrP$^c$.

(iii) Construction of pSH2-1/pEG202-GST-PrP$^c$. A 646-bp DNA fragment coding for amino acids 23 to 231 of the PrP$^c$ protein was amplified by PCR from the cDNA clone pAcSG2T::PrP$^c$23–231. The PrP$^c$ fragment was cloned via BamHI/Sa/I restriction sites into vector pSH2-1-GST, yielding pSH2-1-GST-PrP$^c$. The GST-PrP$^c$ cassette was excised from this vector using the EcoRI and Sa/I restriction sites and cloned into pEG202, resulting in pEG202-GST-PrP$^c$.

(iv) Construction of pSH2-1-PrP$^c$-GST. The PrP$^c$23–231 cassette was amplified by PCR from pAcSG2T::PrP$^c$23–231 and cloned into pSH2-1-GST via the EcoRI restriction site resulting in pSH2-1-PrP$^c$-GST.

Correct orientation, reading frames and sequences of the PCR amplified fragments were confirmed by dideoxy sequencing (41).

EXAMPLE 2
Expression of the 'Bait' Protein LexA-GST-PrP$^c$ in S. cerevisiae Strain EGY48

For 'two-hybrid' screening, a fusion protein 'bait' consisting of the bacterial repressor LexA binding domain (19, 21) and the Syrian Golden Hamster prion protein PrP$^c$23–231 (aa=amino acids 23 to 231, referred to as PrP$^c$) (5) fused to glutathione S-transferase (GST) was tested. As reported recently, fusion with GST significantly enhances the solubility and stability of recombinant PrP$^c$ (47, 48). Cells of the yeast strain EGY48 were cotransformed with the reporter plasmid pSH18-34 and the bait plasmids and tested for their intrinsic ability to activate the reporter system. The pSH-GST-PrP$^c$ construct showed a low level of intrinsic activation. Expression of the LexA-GST-PrP$^c$ fusion protein in S. cerevisiae was confirmed by immunoblotting employing a polyclonal anti-PrP antibody (20) directed against aa 95 to 110 (data not shown).

EXAMPLE 3
Identification of PrPC/Hsp60 Interaction by the Two-hybrid Screen

Detailed procedures for using the yeast two-hybrid system have been detailed previously (1, 6, 19, 21). S. cerevisiae strain EGY48 (MATa ura3 his3 trp1 LEU2::LexAop6-LEU2), which carries a chromosomal insertion of LexA binding sites upstream of the LEU2-gene was used as the recipient host (19, 21). In brief, yeast strain EGY48 was transformed with the reporter plasmid pSH18-34 containing a LexA controlled lacZ gene as a second reporter. S. cerevisiae cells were cotransformed with the 'bait'-plasmid and pJG4–5 containing a HeLa cDNA library fused to the acidic B42 transactivation domain (19, 21). The cDNA insert of the pJG4–5 plasmid is controlled by a galactose inducible promoter. Therefore, interaction between the two hybrids occurs only in the presence of galactose. 2000 Colonies able to grow in the absence of leucine (first reporter gene) were dotted on galactose plates supplemented with 5-bromo-4-chloro-3-indolyl-b-D-galactopyranoside (X-Gal) and screened for b-galactosidase production (blue color, second reporter gene).

cDNAs of 55 positive clones were recovered from 5 ml $S.$ $cerevisiae$ cell cultures. Cells were incubated at 30° C. for 2 days, harvested by centrifugation (3000 rpm, 10 min at 4° C.) and washed (1 M sorbitol, 0,1 M EDTA, pH 8.0). After resuspension in SCE (1 M sorbitol, 0,1 M sodium citrate, pH 5.8, 10 mM EDTA, 0,1 M b-mercaptoethanol) the cells were incubated with 40 ml Lyticase (5 U/ml, Sigma) for 1 h at 37° C. After centrifugation, cells were resuspended in TE-lysis buffer (50 mM Tris/HCl, pH 7.4, 20 mM EDTA containing 1% SDS) and incubated for 30 min at 65° C. The lysate was phenol extracted, the DNA ethanol precipitated and resuspended in TE. The DNA was transformed in $E.$ $coli$ strain KC8 which enables the selection of pJG4–5 plasmids by ampicillin resistance and complementation of its tryptophan auxotrophy (19, 21). As control experiments the plasmids were retransformed in EGY48 and the transformants tested for b-galactosidase production and for their Leu$^+$-phenotype. Five retransformants were dotted on corresponding plates, incubated for 5 days at 30° C. and finally sequenced. cDNA inserts were sequenced with the T7-sequencing kit (Pharmacia) based on the dideoxy method (41). Homology searches for the cDNA sequences were performed at the National Center for Biotechnology Information using the BLAST network service (http://www.ncbi.nlm.nih.gov/Recipon/bs_seq.html). Approx. 20% (corresponding to nine cDNAs) encoded heat shock protein 60 (Hsp60 ). The isolated Hsp60 cDNAs encode for three N-terminally truncated proteins with different lengths starting at position aa 146, aa 228 and aa 298, respectively (EMBL M34664). All of them contain parts of the putative peptide binding domain of Hsp60 (14).

EXAMPLE 4
Test for Specificity of the PrP$^c$/Hsp60 Interaction

Specificity of the observed in vivo interaction between PrP$^c$ and Hsp60 (FIG. 1, row 3) was demonstrated by several recloning experiments. In particular, it was shown that the inverse fusion PrP$^c$::GST (FIG. 1, row 6), as well as authentic PrP$^c$ lacking GST (data not shown) strongly interact with Hsp60. In contrast, LexA-GST (FIG. 1, row 2), authentic LexA (FIG. 1, row 1), as well as the two 'false-baits' LexA-NFl/CTF2 (47) (FIG. 1, row 4) and LexA-bicoid (FIG. 1, row 5) showed no interaction with Hsp60.

EXAMPLE 5
Recombinant Hsp60 Binds Specifically to PrP$^c$23–231 and rPrP27–30 in vitro PrP$^c$23–231 represents the mature form of the cellular prion protein. Scrapie prion isolates consist mainly of the protease-resistant core which is 27 30 kDa in size (referred to as PrP27–30) (35, 42), comprising amino acids 90 to 231. We employed recombinant GST fusion proteins bound to glutathione Sepharose beads to confirm the interaction with recombinant full-length Hsp60 in vitro. GST as well as PrP$^c$23–231 and rPrP27–30 fused to GST (47, 48) were immobilized and incubated with Hsp60. Hsp60 was detected in the presence of GST-PrP$^c$ (FIG. 2A, lane 2), and GST-rPrP27–30 (FIG. 2A, lane 3) but not with GST alone (FIG. 2A, lane 4). Another human chaperone, Hsp70, did not interact with any of these proteins (data not shown) demonstrating that the interaction of PrP$^c$ with Hsp60 is highly specific.

Proteins and antibodies. GST, GST::PrP$^c$23–231, as well as the GST::PrP$^c$ fragments GST::P23–52, GST::P53–93, GST::P90–109, GST::P129–175, GST::P180–210 and GST::P218–231 were prepared as described (48). GST::rPrP27–30 (aa 90 to 231 of the Syrian Golden Hamster prion protein) was expressed in and purified from $E.$ $coli$ and from the baculovirus expression system (47). GroEL and anti-rabbit-IgG-POD as well as anti-mouse-IgG-POD were obtained from Boehringer Mannheim. Recombinant human Hsp60 was provided by StressGen and monoclonal mouse anti-Hsp60 was obtained from Sigma.

SDS PAGE and immunoblotting. Protein samples were analyzed on 12.5% SDS Phastgels (Pharmacia) as described previously (48). Rainbow marker (RPN 756, Amersham) was used as a size standard. Following electrophoresis, gels were blotted onto nitrocellulose (NC, Schleicher & Schuell) or polyvinyldifluoride membranes (PVDF, Millipore) (40 min. at 70° C.). The blots were incubated with a polyclonal anti-GroEL or anti-PrP antibody at 1:800/1:400 dilutions. Incubation steps were performed as described previously (44). Antibody detection was performed by chemiluminescence (ECL system, Amersham) or in the presence of DAB (Sigma).

EXAMPLE 6
Binding of the Bacterial GroEL to PrPC23–231 and rPrP27–30 in vitro.

To investigate whether GroEL, the prokaryotic homologue of the Hsp60 family is also capable of binding to PrP$^c$, recombinant GroEL in corresponding in vitro binding experiments was employed. Pull-down assays were performed by equilibrating glutathione-Sepharose 4B beads (Pharmacia) loaded with GST or the GST fusion protein in refolding buffer (RF) (32) including 0.5% Triton-X-100. The equilibrated beads were incubated with an up to 10 fold molar excess of GroEL or Hsp60 (monomer) at room temperature in the presence of RF including 0.5% Triton-X-100. After centrifugation (2500 rpm, 10 min) the beads were washed with RF and analyzed on a 12.5% SDS Phastgel, blotted and probed for the presence of GroEL or Hsp60.

GroEL was found to exhibit specificity in the interaction with PrP$^c$ (FIG. 2B, lane 3) and rPrP27–30 (FIG. 2C, lane 2) fused to GST whereas no binding occurs in the presence of GST alone (FIG. 2B, lane 4 and FIG. 2C, lane 3). However, the strength of binding is stronger for rPrP27–30 compared to PrP$^c$.

EXAMPLE 7
Mapping of the Interaction Site for Hsp60 and GroEL within PrP

To obtain a comprehensive map of the PrP$^c$-binding site on the molecular chaperones six fragments of PrP fused to GST were employed and their ability to bind Hsp60 and GroEL was tested. These peptides were designed on the basis of biochemical predictions regarding hydrophilicity, antigenicity and secondary structure (48) and represent aa 23 to 52, aa 53 to 93, aa 90 to 109, aa 129 to 175, aa 180 to 210 and aa 218 to 231 (FIG. 3A). The immobilized peptides were incubated with Hsp60 and GroEL, respectively. This mapping analysis identified Hsp60 (FIG. 3B, lane 6) and GroEL (FIG. 3C, lane 6) only in the presence of GST::P180–210, demonstrating that it is only the PrP region represented by amino acids 180 to 210 which interacts with the molecular chaperone.

EXAMPLE 8
Downregulation of Hsp60 in the Presence of Hamster PrP$^c$23–231 in the Fusion with GST FLAG tagged Hsp60 has been synthesized as a 61 kDA protein in the baculovirus system (FIG. 4, lane 1). Co-expression of GST::rPrP$^c$ (rPrP23–231) (lane 3) and GST::rPrP27–30 (rPr90–231) (lane 4) down regulates FLAG::Hsp60 expression, whereas co-expression of GST does not affect expression of FLAG::Hsp60 (lane 2).

Co-infection was carried out followed by Western Blot analysis. Total protein was harvested from baculovirus infected insect cells by standard methods and analyzed by SDS-PAGE. The following Western Blot employed an anti-Hsp60 antibody (Sigma # H 4149).

The down regulation of Hsp60 in the presence of PrP$^c$ can occur either on transcription or translational level. Alternatively, PrP could trigger proteolytic degradation of Hsp60. Finally, PrP$^c$ could lead to an increased secretion process of Hsp60. The presence of Hsp60 in the culture medium would prove this hypothesis. Down regulation of Hsp60 in the presence of PrP can account for a direct PrP/Hsp60 interaction which leads to an increased down regulation of Hsp60. Application of PrP-peptides spanning parts of the prion protein can identify the region of the prion protein which is responsible for the down regulation of Hsp60 expression.

CITED REFERENCES

1. Altmann, H., W. Wendler and E.-L. Winnacker. Transcriptional activation by CTF proteins is mediated by a bipartite low-proline domain. Proc. Natl. Acad. Sci. USA. 91 (1994), 3901–3905.
2. Aiken, J. M., J. L. Williamson and R. F. Marsh. Evidence for Mitochondrial Involvement in Scrapie Infection. J. Virol. 63 (1989), 1686–1694.
3. Alper, T., D. A. Haig and M. C. Clarke. The exceptionally small size of the scrapie agent. Biochem. Biophys. Res. Commun. 22 (1966), 278–284.
4. Alper, T., W. A. Cramp, D. A. Haig and M. C. Clarke. Does the agent of scrapie replicate without nucleic acid? Nature 214 (1967), 764–766.
5. Basler, K., B. Oesch, M. Scott, D. Westaway, M. Walchli, D. F. Groth, M. P. McKinley, S. B. Prusiner and C. Weissmann. Scrapie and cellular PrP isoforms are encoded by the same chromosomal gene. Cell 46 (1986), 417–428.
6. Benson, J. D. and P. M. Howley. Amino-Terminal Domains of the Bovine Papillomavirus Type 1 E1 and E2 Proteins Paticipate in Complex Formation. J. Virol. 69 (1995), 4364–4372.
7. Bessen, R. A., D. A. Kocisko, G. J. Raymond, S. Nandan, P. T. Lansbury and B. Caughey. Non-genetic propagation of strain-specific properties of scrapie prion protein. Nature 375 (1995),698–700.
8. Borchelt, D. R., A. Taraboulos and S. B. Prusiner. Evidence for synthesis of scrapie prion proteins in the endocytic pathway. J. Biol. Chem. 267 (1992), 16188–16199.
9. Borchelt, D. R., M. Scott, A. Taraboulos, N. Stahl and S. B. Prusiner. Scrapie and cellular prion proteins differ in their kinetics of synthesis and topology in cultured cells. J. Cell Biol. 110 (1990), 743–752.
10. Braig, K., Z. Otwinowski, R. Hedge, D. C. Boisvert, A. Joachimiak, A. L. Horwich and P. B. Sigler. The crystal structure of the bacterial chaperonin GroEL at 2.8 Å. Nature 371 (1994), 578–586.
11. Caughey, B. and G. J. Raymond. The scrapie-associated form of PrP is made from a cell surface precursor that is both protease- and phospholipase-sensitive. J. Biol. Chem. 266 (1991), 18217–18223.
12. Chernoff, Y. O., S. L. Lindquist, B.-i. Ono, S. G. Inge-Vechtomov and S. W. Liebman. Role of the Chaperone Protein Hsp104 in Propagation of the Yeast Prion-Like Factor [psi$^+$]. Science 268 (1995), 880–884.
13. Ellis J. Proteins as molecular chaperones. Nature 328 (1987), 378–379.
14. Fenton, W. A., Y. Kashi, K. Furtak and A. L. Horwich. Residues in chaperonin GroEL required for polypeptide binding and release. Nature 371 (1994), 614–619.
15. Fields, S. and K.-O. Song. A novel genetic system to detect proteinprotein interactions. Nature 340 (1989), 245–246.
16. Ganea, E. and J. J. Harding. Molecular chaperones protect against glycation-induced inactivation of glucose-6-phosphate dehydrogenase. Eur. J. Biochem. 231 (1995) 181–185.
17. Gasset, M., M. A. Baldwin, R. J. Fietterick and S. B. Prusiner. Perturbation of the secondary structure of the scrapie prion protein under conditions that alter infectivity. Proc. Natl. Acad. Sci. USA. 90 (1993), 1–5.
18. Gething, M.-J. and J. Sambrook. Protein folding in the cell. Nature 355 (1992), 33–45.
19. Golemis, E. A., J. Gyuris and R. Brent. Interaction Trap/Two-Hybrid System to identify interacting proteins. in Current Protocols in Mol. Biol., (Ausubel etal. ed.) (1994) pp 13.14.1–13.14.17, Wiley & Sons.
20. Groschup, M. H., J. Langeveld and E. Pfaff. The major species specific epitope in prion proteins of ruminants. Arch. Virol. 136 (1994), 423–431.
21. Gyuris, J., E. Golemis, H. Chertkov and R. Brent. Cdi1, a Human G1 and S Phase Protein Phosphatase That Associates with Cdk2. Cell 75 (1993), 791–803.
22. Hartl, F. U. and J. Martin. Molecular chaperones in cellular protein folding. Curr. Opinion Struct. Biol. 5 (1995), 92–102.
23. Hartl, F. U., J. Martin and W. Neupert. Protein Folding in the Cell: The Role of Molecular Chaperones Hsp70 and Hsp60. Ann. Rev. Biophys. Biomol. Sruct. 21 (1992), 293–322.
24. Huang, Z., J.-M. Gabriel, M. A. Baldwin, R. J. Fletterick, S. B. Prusiner and F. E. Cohen. Proposed three-dimensional structure for the cellular prion protein. Proc. Natl. Acad. Sci. USA. 91 (1994), 7139–7143.
25. Itoh, H., R. Kobayashi, H. Wakui, A. Komatsuda, H. Ohtani, A. B. Miura, M. Otaka, O. Masamune, H. Andoh, K. Koyama, Y. Sato and Y. Tashima. Mammalian 60-kDa Stress Protein (Chaperonin Homolog). Identification, Biochemical Properties and Localization. J. Biol. Chem. 270 (1995), 13429–13435.
26. Kazmirski, S. L., D. O. V. Alonso, F. E. Cohen, S. B. Prusiner and V. Daggett. Theoretical studies of sequence effects on the conformational properties of a fragment of the prion protein: implications for scrapie formation. Chemistry & Biology 2 (1995), 305–315.
27. Kocisko, D. A., S. A. Priola, G. J. Raymond, B. Chesebro, P. T. Jr. Lansbury and B. Caughey. Species specifity in the cell-free conversion of prion protein to protease-resistant forms: A model for the scrapie species barrier. Proc. Natl. Acad. Sci. USA. 92 (1995), 3923–3927.

28. Kocisko, D. A., J. H. Come, S. A. Priola, B. Chesebro, G. J. Raymond, P. T. Lansbury and B. Caughey. Cell-free formation of protease-resistant prion protein. Nature 370 (1994), 471–474.
29. Lansbury, P. T. Jr. and B. Caughey. The chemistry of scrapie infection: implications of the 'ice 9' metaphor. Chemistry & Biology 2 (1995), 1–5.
30. Nguyen, J., M. A. Baldwin, F. E. Cohen and S. B. Prusiner. Prion Protein Peptides Induce α-helix to β-sheet Conformational Transitions. Biochemistry 34 (1995), 4186–4192.
31. Pan, K.-M., M. Baldwin, J. Nguyen, M. Gasset, A. Serban, D. Groth, I. Mehlhorn, Z. Huang, R. J. Fletterick, F. E. Cohen and S. B. Prusiner. Conversion of α-helices into β-sheets features in the formation of the scrapie prion proteins. Proc. Natl. Acad. Sci. USA 90 (1993), 10962–10966.
32. Phadtare, S., M. T. Fisher and L. R. Yarbrough. Refolding and release of tubulins by a functional immobilized groEL column. Biochim. et Biophys. Acta 1208 (1994), 189–192.
33. Prusiner, S. B. and K. K. Hsiao. Human prion diseases. Ann. Neurol. 35 (1994), 385–395.
34. Prusiner, S. B. Molecular biology of prion disease. Science 252 (1991), 1515–1522.
35. Prusiner, S. B., D. F. Groth, D. C. Bolton, S. B. Kent and L. E. Hood. Purification and structural studies of a major scrapie prion protein. Cell 38 (1984), 127–134.
36. Prusiner, S. B. Novel proteinaceous infectious particles cause Scrapie. Science 216 (1982), 136.
37. Ross, W. R., W. S. Bertrand and A. R. Morrison. Identification of a processed protein related to the human chaperonins (hsp 60) protein in mammalian kidney. Biochem. Biophys. Res. Commun. 185 (1992), 683–687.
38. Safar, J., P. P. Roller, D. C. Gajdusek and C. J. Jr. Gibbs. Conformational transitions, dissociation, and unfolding of scrapie amyloid (prion) protein. J. Biol. Chem. 268 (1993), 20276–20284.
39. Saiki, R. K., D. H. Gelfand, S. Stoffel, S. J. Scharf, R. Higuchi, G. T. Horn, K. B. Mullis and Erlich, H. A. Primer-directed enzymatic amplification of DNA with a thermostable DNA polymerase. Science 239 (1988), 487–491.
40. Sambrook J., E. F. Fritsch and T. Maniatis. Molecular Cloning. A Laboratory Manual, 2nd ed. Cold Spring Harbor Laboratory Press, Cold Spring Harbor, N.Y., 1989.
41. Sanger, F., S. Nicklen and A. R. Coulson. DNA sequencing with chain terminating inhibitors. Proc. Natl. Acad. Sci. USA 74 (1977), 5463–5467.
42. Stahl, N., M. A. Baldwin, D. B. Teplow, L. Hood, B. W. Gibson, A. L. Burlingame and S. B. Prusiner. Structural studies of the scrapie prion protein using mass spectrometry and amino acid sequencing. Biochemistry 32 (1993), 1991–2002.
43. Telling, G. C., M. Scott, J. Mastrianni, R. Gabizon, M. Torchia, F. E. Cohen, S. J. DeArmond and S. B. Prusiner. Prion Propagation in Mice Expressing Human and Chimeric PrP Transgenes Implicates the Interaction of Cellular PrP with Another Protein. Cell 83 (1995), 79–90.
44. Towbin, H., T. Staehelin and J. Gordon. Electrophoretic transfer of proteins from polyacrylamide gels to nitrocellulose sheets: procedure and some applications. Proc. Natl. Acad. Sci. USA 76 (1979), 4350–4354.
45. Velez-Granell, C. S., A. E. Arias, J. A. Torres-Ruiz and M. Bendayan. Molecular chaperones in pancreatic tissue: the presence of cpn10, cpn60 and hsp70 in distinct compartments along the secretory pathway of the acinar cells. J. Cell. Sci. 107 (1994), 539–549.
46. Vitek, M. P., K. Bhattacharya, J. M. Glendening, E. Stopa, H. Viassara, R. Bucala, K. Manogue and A. Cerami. Advanced glycation end products contribute to amyloidosis in Aizheimer disease. Proc. Natl. Acad. Sci. USA. 91 (1995), 4766–4770.
47. Weiss, S., R. Rieger, F. Edenhofer, E. Fisch and E.-L. Winnacker. Recombinant prion protein rPrP27–30 from the Syrian Golden Hamster reveals protease K sensitivity. Biochem. Biophys. Res. Commun. 219 (1996), 173–179.
48. Weiss, S., M. Famulok, F. Edenhofer, Y.-H. Wang, I. M. Jones, M. Groschup and E.-L. Winnacker. Overexpression of Active Syrian Golden Hamster Prion Protein $PrP^c$ as a Glutathione S-Transferase Fusion in Heterologous Systems. J. Virol. 69 (1995), 4776–4783.
49. Wendler, W., H. Altmann and E.-L. Winnacker. Transcriptional activation of NFIlCTF1 depends on a sequence motif strongly related to the carboxyterminal domain of RNA polymerase II. Nucl. Acids Res. 22 (1994), 2601–2603.
50. Wickner, R. B. Prions of yeast and heat-shock protein 104: 'coprion' and cure. Trends in Microbiol. 3 (1995), 367–369.
51. Sambrook J., Fritsch, E. F., and Maniatis, T. Molecular Cloning. A Laboratory Manual, 2nd ed. Cold Spring Harbor Laboratory Press (1989). Cold Spring Harbour, N.Y.
52. Redl, B., Walleczek, J., Stoffler-Meilicke, M. and Stoffler, G. Immunoblotting analysis of protein-protein crosslinks within the 50S ribosomal subunit of E. coli: A study using dimethylsuberimidate as crosslinking reagent. Eur. J. Biochem. 181 (1989), 351–356.
53. Maurer, H. Disc electrophoresis and related techniques of polyacrylamide gel electrophoresis. Walter de Gruyter (1971), Berlin/N.Y.
54. Hummel, J. P. and Dreyer, W. J. Measurement of protein binding phenomenon by gel filtration. Biochem. Biophys. Acta 63 (1962), 530–532.
55. Le-Grice, S. F. and Gruninger-Leitch. F. Rapid purification of homodimer and heterodimer HIV-1 reverse transcriptase by metal chelate affinity chromatography. Eur. J. Biochem. 187 (1990), 307–314.
56. Carr, D. W., Stofko-Hahn, R. E., Fraser, I. D. C., Bishop, S. M., Acott, T. S., Brennan, R. G. and Scott, J. D. Interaction of the regulatory subunit (RII) of cAMP-dependent protein kinase with RII-anchoring proteins occurs through an amphipathic helix binding motif. J. Biol. Chem. 266 (1991), 14188–14192.
57. Kim, J. S. and Raines, R. T. Ribonuclease S-peptide as a carrier in fusion proteins. Protein Sci. 2 (1993), 348–356.
58. Kawase, M., Mornoeda, M., Young, N. S. and Kijagaya, S. Most of the VP1 unique region of B19 parvovirus is on the capsid surface. Virology 211 (1995), 359–366.
59. Wang, L.-F., Yu,, M., White, J. R. and Eaton, B. T., BTag: a novel six-residue epitope tag for surveillance and purification of recombinant proteins. Gene 169 (1996), 53–58.
60. Aitken, R., Gilchrist, J. and Sinclair, M. C. Vectors to facilitate the creaton of translational fusions to the maltose-binding protein of *Escherichia coli.* Gene 144, (1994) 69–73.
61. Richards, F. M. and Wyckoff, H. W. in "The Enzymes" Vol. IV (Boyer, P. D., Ed.) (1971), 647–806, Academic Press, New York.
62. Carr, D. W. and Scott, J. D. Blotting and band-shifting: Techniques for studying protein-protein interactions. Trends Biochem. Sci. 17, (1992) 246–249.
63. Dean, P. D. G., Johnson, V. S. and Middle, F. A., Eds., IRL Press, Oxford, England (1985), 215.
64. Prusiner, S. B., McKinley, M. P., Bowman, K. A., Bolton, D. C., Bendheim, P. E., Groth, D. F., and Glenner, G. G. Scrapie prions aggregate to form amyloid-like birefringent rods. Cell 35 (1983), 349–358.
65. Hampton, R. Y. Koning, A., Wright, R. and Rine, J. In-vivo examination of membrane protein localization and degradation with green fluorescent protein. PNAS 93 (1996), 828–833.
66. Formosa, T., Barry, J., Alberts, B. U. and Greenblatt, J. Using protein affinity chromatography to probe structure of protein machines. Methods Enzymol. 208 (1991), 24–45.
67. Tatzelt, J., Prusiner, S. B., and Welch, W. J. Chemical chaperones interfere with the formation of scrapie prion protein. Embo J. 15 (1996), 6363–73.

What is claimed is:

1. A method of detecting a prion protein comprising the steps of:
   (a) contacting a probe suspected to contain a prion protein with at least one partner protein comprising hsp60 or GroEL,
   (b) by said contacting, forming a complex of said prion protein in said probe with said at least one partner protein, and
   (c) detecting the presence of said prion protein that forms such a complex with said at least one partner protein by detecting the presence of said complex.

2. The method of claim 1, wherein said detecting includes isolating said prion protein bound to said at least one partner protein.

3. The method of claim 1, wherein said at least one partner protein is part of a fusion protein.

4. The method of claim 3, wherein said fusion protein includes at least a portion of glutathione-S-transferase, FLAG, oligohistidine, GFP, CBP, MBP, Btag or S-peptide of ribonuclease A.

5. The method of claim 1, wherein said prion protein is $Prp^c$, or a fragment thereof that binds to said at least one partner protein.

6. The method of claim 1, wherein said prion protein is $Prp^{sc}$, or a fragment thereof that binds to said at least one partner protein.

7. The method of claim 1, wherein said prion protein is $PrP^C$23–231, PrP27–30, or a fragment thereof that binds to said at least one partner protein.

8. The method of claim 1, wherein said at least one partner protein contains a detectable label.

9. The method of claim 8, wherein said label is a radioisotope, fluorescent compound, colloidal metal, chemiluminescent compound, bioluminescent compound, phosphorescent compound or an exzyme.

10. The method of claim 1, wherein said at least one partner protein is bound to a solid phase.

11. The method of claim 10, wherein said solid phase is glutathione-SEPHAROSE, anti-FLAG-antibody, NAC-$Ni^{21}$, anti-GEP-antibody, anti-BFag-antibody, caimodulin, S-protein 104aa or maltose.

12. The method of claim 10, wherein said at least one partner protein is part of a matrix affinity chromatography column, and step (b) includes passing said probe through said column.

13. The method of claim 1, wherein said probe is obtained from brain, ileum, cortex, dura mata, Purkinje cells, lymph nodes, nerve cells, spleen, tonsils, muscle cells, placenta, pancreas, eyes, backbone marrow, or Peyer's patches.

14. The uethiod of claim 13, wherein said probe is from a body fluid.

15. The method of claim 14, wherein said body fluid is from blood, cerebrospinal fluid, semen or milk.

16. The method of clam 1, for in vitro diagnosis of a transmissible spongiform encephalopathy, wherein step (b) includes determining whether or not an isoform of $PrP^c$ is present in a sample.

17. The method of claim 1, wherein said at least one partner protein is human Hsp60.

18. The method of claim 1, wherein said at least one partner protein is GroEL.

* * * * *